United States Patent
Philippe et al.

(10) Patent No.: US 6,924,275 B2
(45) Date of Patent: *Aug. 2, 2005

(54) AMINOPHENOL DERIVATIVES AND THEIR USE IN COSMETICS

(75) Inventors: Michel Philippe, Wissous (FR); Remy Tuloup, Paris (FR); Christian Blaise, Saint Mande (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/125,411

(22) Filed: Apr. 19, 2002

(65) Prior Publication Data

US 2002/0161040 A1 Oct. 31, 2002

Related U.S. Application Data

(63) Continuation of application No. 09/284,490, filed as application No. PCT/FR98/01856 on Aug. 26, 1998, now Pat. No. 6,423,854.

(30) Foreign Application Priority Data

Aug. 27, 1997 (FR) .......................................... 97 10710

(51) Int. Cl.⁷ .............................................. A61K 31/56
(52) U.S. Cl. .................................................... 514/182
(58) Field of Search .......................... 514/182; 552/502, 552/544; 564/305; 568/706

(56) References Cited

U.S. PATENT DOCUMENTS 6,423,854 B1 * 7/2002 Philippe et al. ............. 552/544

FOREIGN PATENT DOCUMENTS

| EP | 0 709 225 | * | 5/1996 |
| JP | 6-344672 | * | 12/1994 |
| JP | 7-223366 | * | 8/1995 |

OTHER PUBLICATIONS

STN/CAS online, file Beilstein, Record No. 3183408 (1991), Abstract.*
File CAPLUS, STN/CAS online, Acc. No. 1975:571084, Doc. No. 83:171084 (Verbit et al., "Synthesis and liquid crystal properties of some urethanes," Molecular Crystals and Liquid Crystals (1975), vol. 30, No. 1–2, pp. 87–99), Abstract.*
File CAPLUS, STN/CAS online, Acc. No. 1992:117817, Doc. No. 116:117817 (Vora et al., "Cholesteryl dicarbonates with rigid and flexible spacers," Molecular Crystals and Liquid Crystals (1991), vol. 209, pp. 285–289), Abstract.*

* cited by examiner

Primary Examiner—S. Mark Clardy
Assistant Examiner—Frank Choi
(74) Attorney, Agent, or Firm—Oblon, Spivak, McClelland, Maier & Neustadt, P.C.

(57) ABSTRACT

Use of at least one aminophenol derivative of formula (I) below:

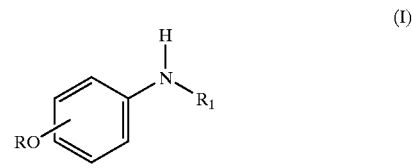

in which:

R represents a hydrogen atom or a radical —$COR_2$, wherein $R_2$ represents a saturated or unsaturated, linear, cyclic or branched, optionally hydroxylated, $C_1$ to $C_{30}$ hydrocarbon or alkoxy radical;

$R_1$ is a radical of formula (a), (b) or (c) below:
(a) —CO—$NR_3R_4$
(b) —CO—O—$R_5$
(c) —$SO_2$—$R_5$ wherein $R_3$ represents a hydrogen atom or a linear or branched, saturated or unsaturated, optionally hydroxylated, $C_1$ to $C_4$ hydrocarbon radical, $R_4$ represents a hydrogen atom or a saturated or unsaturated, linear, cyclic or branched, optionally hydroxylated, $C_1$ to $C_{30}$ hydrocarbon radical, and $R_5$ represents a saturated or unsaturated, linear, cyclic or branched, optionally hydroxylated, $C_1$ to $C_{30}$ hydrocarbon radical, in a depigmenting and/or bleaching cosmetic composition for human skin, body hairs or head hair; compositions comprising the derivatives of formula (I) and a process for depigmenting and/or bleaching the skin, body hairs and/or head hairs.

18 Claims, No Drawings

AMINOPHENOL DERIVATIVES AND THEIR USE IN COSMETICS

The present invention relates to the use of aminophenol derivatives as depigmenting or bleaching agents in a cosmetic and/or dermatological composition, to a cosmetic and/or dermatological composition comprising these derivatives and to novel aminophenol derivatives.

The colour of the skin depends on different factors and, in particular, the seasons of the year, race and sex, and it is mainly determined by the type and concentration of melanin produced by the melanocytes. Melanocytes are specialized cells which synthesize melanin by means of specific organelles, the melanosomes. In addition, at different periods in their life, certain individuals develop darker and/or more coloured blemishes on the skin and more especially on the hands, making the skin non-uniform. These blemishes are also due to a large concentration of melanin in the keratinocytes at the skin surface.

In the same way, the colour of body hairs and head hair is due to melanin. When hairs or head hair are dark, certain people wish to have them lighter. This is particularly advantageous for hairs which are less visible when they are light than when they are dark.

The mechanism for the formation of skin pigmentation, and pigmentation of body hairs and head hair, that is to say the formation of melanin, is particularly complex and schematically involves the following main steps:

Tyrosine—Dopa—Dopaquinone—Dopachrome—Melanin

Tyrosinase (monophenol dihydroxyl phenylalanine: oxygen oxidoreductase EC 1.14.18.1) is the essential enzyme involved in this reaction sequence. It especially catalyses the reaction for the conversion of tyrosine into dopa (dihydroxyphenylalanine), by virtue of its hydroxylase activity, and the reaction for the conversion of dopa into dopaquinone. This tyrosinase acts only when it is in the mature state, under the action of certain biological factors.

A substance is recognized as being depigmenting if it acts directly on the vitality of the epidermal melanocytes in which melanogenesis takes place and/or if it interferes with one of the steps in the biosynthesis of melanin either by inhibiting one of the enzymes involved in melanogenesis or by becoming intercalated as a structural analogue of one of the chemical compounds in the melanin synthesis chain, whereby this chain may be blocked and ensure the depigmentation.

The substances most commonly used as depigmenting agents are, more particularly, hydroquinone and its derivatives, in particular its ethers such as hydroquinone monomethyl ether and monoethyl ether. Although they have a certain level of efficacy, these compounds are unfortunately not free of side effects on account of their toxicity, which can make them difficult or even hazardous to use. This toxicity arises from the fact that they interfere with fundamental mechanisms of melanogenesis, by killing cells which then risk disrupting their biological environment and which consequently force the skin to eliminate them by producing toxins.

Thus, hydroquinone is a compound which is particularly irritant and cytotoxic to melanocytes, and whose total or partial replacement has been envisaged by many authors.

Substances have thus been sought which are not involved in the mechanism of melanogenesis, but which act upstream on tyrosinase by preventing its activation, and are consequently much less toxic. Kojic acid is commonly used as tyrosinase-activation inhibitor, this acid complexing the copper present in the active site of this enzyme. Unfortunately, this compound can give rise to allergic reactions ("Contact allergy to kojic acid in skin care products", Nakagawa M. et al., in Contact Dermatitis, January 95, Vol 42 (1), pp. 9–13). In addition, this compound is unstable in solution, which somewhat complicates the manufacture of the composition.

It is most particularly sought to use harmless topical depigmenting substances which are of good efficacy, in order to treat regional hyperpigmentations caused by melanocyte hyperactivity, such as idiopathic melasmas, occurring during pregnancy ("pregnancy mask" or chloasma) or during oestro-progestative contraception, localized hyperpigmentations caused by hyperactivity and proliferation of benign melanocytes, such as senile pigmentation marks known as actinic lentigo, accidental hyperpigmentations or depigmentations, possibly due to photosensitization or to post-lesional cicatrization, as well as certain leukodermias, such as vitiligo. For the latter, in which the cicatrizations can result in a scar which gives the skin a whiter appearance and leukodermias, failing being able to repigment the damage to the skin, the regions of residual normal skin are depigmented in order to give the skin as a whole a uniform white complexion.

Thus, there is a need for a novel agent for bleaching human skin, hairs and/or head hair which acts as effectively as the known agents, but which does not have their drawbacks, i.e. which is non-irritant, non-toxic and/or non-allergenic to the skin and which is stable in a composition.

The Applicant has found, unexpectedly, that aminophenol derivatives have depigmenting activity, even at low concentrations, without showing any cytotoxicity.

Some of these derivatives are already known from U.S. Pat. No. 2,663,730, U.S. Pat. No. 3,933,470, GB-A-1,205, 029, DD 107,449 or from A. Etienne et al. "Isocyanurates diméthylés-1.3 et arylés-5 [1,3-dimethyl and 5-aryl isocyanurates]", Comptes rendus hebdomadaires des séances de l'académie des sciences, Série C: sciences chimiques, Vol. 279, Dec. 2, 1974, pp. 969–972, for example. Other aminophenol derivatives have been discovered by the Applicant.

The subject of the present invention is thus the use of at least one aminophenol derivative of formula (I) below:

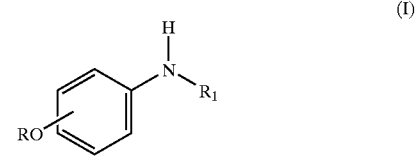

(I)

in which:
R represents a hydrogen atom or a radical —$COR_2$,
wherein $R_2$ represents a saturated or unsaturated, linear, cyclic or branched, optionally hydroxylated, $C_1$ to $C_{30}$ hydrocarbon or alkoxy radical;
$R_1$ is a radical of formula (a), (b) or (c) below:
(a) —CO—$NR_3R_4$
(b) —CO—O—$R_5$
(c) —$SO_2$—$R_5$
wherein $R_3$ represents a hydrogen atom or a linear or branched, saturated or unsaturated, optionally hydroxylated, $C_1$ to $C_6$ hydrocarbon radical,
$R_4$ represents a hydrogen atom or a saturated or unsaturated, linear, cyclic or branched, optionally hydroxylated, $C_1$ to $C_{30}$ hydrocarbon radical,
$R_5$ represents a saturated or unsaturated, linear, cyclic or branched, optionally hydroxylated, $C_1$ to $C_{30}$ hydrocarbon radical, in a depigmenting and/or bleaching cosmetic composition for human skin, body hairs or head hair.

These compositions have the advantage of being easy to obtain. They can be obtained in particular by reacting an aminophenol with an activated chemical species, such as an imidazolide or an isocyanate when $R_1$ is a radical of formula (a), a chloroformate when $R_1$ is a radical of formula (b) or a sulphonyl chloride when $R_1$ is a radical of formula (c)

The hydrocarbon radicals typically alkyl radicals. Among the linear or branched hydrocarbon radicals having from 1 to 30 carbon atoms, mention may be made advantageously of methyl, ethyl, propyl, isopropyl, butyl, tert-butyl, hexyl, octyl, nonyl, 2-ethylhexyl and dodecyl radicals. Preferably, these radicals have from 1 to 12 carbon atoms. Even more preferably, the hydrocarbon radical generally comprises from 1 to 6 carbon atoms. As lower hydrocarbon radicals, mention may be made of alkyl radicals, for example methyl, ethyl, propyl, isopropyl, tert-butyl and hexyl radicals.

Among the linear alkyl radicals having from 1 to 30 carbon atoms, mention may be made in particular of methyl, ethyl, propyl, octyl, dodecyl, tridecyl, hexadecyl, behenyl, octadecyl, tetracosyl, hexacosyl, octacosyl and myricyl radicals.

Among the branched alkyl radicals having from 1 to 30 carbon atoms, mention may be made in particular of 2-ethylhexyl, 2-butyloctyl and 2-hexyldecyl radicals.

When it is unsaturated, a radical having one or more ethylenic unsaturations is preferred, such as the neryl, 2-nonyl-2-butenyl and 6-(1,3-pentadienyl)-2,4,7-dodecanetrien-9-ynyl radicals and more particularly the allyl radical.

When the alkyl radical is cyclic, mention may be made in particular of the cyclohexyl, cholesteryl or tert-butylcyclohexyl radical.

When it is hydroxylated, the radical preferably comprises 1 to 6 carbon atoms and 1 to 5 hydroxyl groups.

Among the monohydroxyalkyl radicals, the preferred radical is one preferably containing 1 or 3 carbon atoms, in particular the hydroxymethyl, 2-hydroxyethyl and 2- or 3-hydroxypropyl radicals.

Among the polyhydroxyalkyl radicals, the preferred radical is one having from 3 to 6 carbon atoms and from 2 to 5 hydroxyl groups, such as the 2,3-dihydroxypropyl, 2,3,4-trihydroxybutyl, 2,3,4,5-tetrahydroxypentyl and 2,3,4,5,6-pentahydroxyhexyl radicals.

The alkoxy radicals are hydrocarbon radicals, typically alkyl radicals, in particular as described above, preceded by an oxygen atom.

Preferably, the aminophenol derivatives of the present invention are those for which at least one, and preferably all, of the conditions below are satisfied:

R represents a hydrogen atom, the function —OR on the phenyl radical is in an ortho position or, advantageously, in the para position, $R_1$ is chosen from a radical of formula (a) or (b).

The compounds of formula (I) are chosen more particularly from N-ethyloxycarbonyl-4-aminophenol; N-ethyloxycarbonyl-O-ethyloxycarbonyl-4-aminophenol; N-cholesteryloxycarbonyl-4-aminophenol and N-ethylaminocarbonyl-4-aminophenol.

The subject of the present invention is also cosmetic and/or dermatological compositions comprising at least one aminophenol derivative of formula (I) and a cosmetically and/or dermatologically acceptable medium. This composition is particularly intended for topical use on the skin and/or its exoskeleton (head hair, body hairs and the nails).

This cosmetic or dermatological composition is advantageously intended for depigmenting and/or bleaching human skin and/or for removing pigmentation marks from the skin and/or for depigmenting body hairs and/or head hair.

The subject of the present invention is also the use of these aminophenol derivatives in and/or for the manufacture of a cosmetic and/or dermatological composition, as a tyrosinase inhibitor and/or as an inhibitor of melanin synthesis and/or as a depigmenting and/or bleaching agent for the skin, body hairs or head hair.

The subject of the present invention is also novel aminophenol derivatives of formula (I) below:

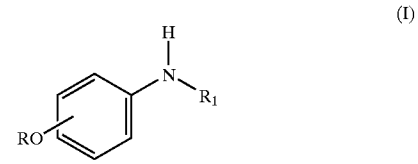

(I)

in which:

R represents a hydrogen atom or a radical —$COR_2$, wherein $R_2$ represents a saturated or unsaturated, linear, cyclic or branched, optionally hydroxylated, $C_1$ to $C_{30}$ hydrocarbon or alkoxy radical;

$R_1$ is chosen from:

(a) a radical —CO—$NR_3R_4$, (b) a cholesteryloxycarbonyl radical, and (c) a radical —$SO_2$—$R_6$ wherein $R_3$ represents a hydrogen atom or a linear or branched, saturated or unsaturated, optionally hydroxylated, $C_1$ to $C_6$ hydrocarbon radical, $R_4$ represents a saturated or unsaturated, linear, cyclic or branched, optionally hydroxylated, $C_{13}$ to $C_{30}$ hydrocarbon radical, and $R_5$ represents a saturated or unsaturated, linear, cyclic or branched, optionally hydroxylated, $C_1$ to $C_{30}$ hydrocarbon radical.

The present invention also relates to a cosmetic process for depigmenting and/or bleaching human skin, body hairs or head hair, this process consisting in applying a cosmetic composition according to the invention to the skin, body hairs or head hair.

The composition according to the invention is suitable for topical use and thus contains a cosmetically or dermatologically acceptable medium, i.e. one which is compatible with the skin, body hairs or head hair.

The aminophenol derivatives will be used in an effective amount to obtain the desired depigmenting or bleaching effect and this amount will depend on the nature of the aminophenol derivatives in question. In particular, the aminophenol derivatives of formula (I) can be present, in particular, in the composition in an amount ranging from 0.001 to 10%, and preferably from 0.005 to 5%, of the total weight of the composition.

The composition of the invention may be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, these spherules possibly being polymeric nanoparticles such as nanospheres and nanocapsules or better still lipid vesicles of ionic and/or non-ionic type.

This composition may be relatively fluid and have the appearance of a white or coloured cream, an ointment, a milk, a lotion, a serum, a paste or a foam. It may optionally be applied to the skin or to the hair in aerosol form. It may also be in solid form and, for example, in the form of a stick. It can be used as a care product and/or as a make-up product. It can also be in the form of a shampoo or a conditioner.

In a known manner, the composition of the invention can also contain the usual adjuvants in the cosmetics and dermatological fields, such as hydrophilic or lipophilic gelling agents, hydrophilic or lipophilic active agents, preserving agents, antioxidants, solvents, fragrances, fillers, screening agents, pigments, odour adsorbers and dyestuffs. The amounts of these various adjuvants are those used conventionally in the fields considered, and, for example, from 0.01 to 20% of the total weight of the composition. Depending on their nature, these adjuvants can be introduced into the fatty phase, into the aqueous phase, into lipid vesicles and/or into nanoparticles.

When the composition of the invention is an emulsion, the proportion of the fatty phase can range from 5 to 80% by weight, and preferably from 5 to 50% by weight, relative to the total weight of the composition. The oils, the emulsifiers and the co-emulsifiers used in the composition in emulsion form are chosen from those used conventionally in the field considered. The emulsifier and the co-emulsifier are present in the composition in a proportion ranging from 0.3 to 30% by weight, and preferably from 0.5 to 20% by weight, relative to the total weight of the composition.

As oils which can be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol) fatty acids and waxes (carnauba wax, ozokerite) can also be used as fatty substances.

As emulsifiers and co-emulsifiers which can be used in the invention, mention may be made, for example, of fatty acid esters of polyethylene glycol, such as PEG 20 stearate, and fatty acid esters of glycerol, such as glyceryl stearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Polyols (glycerol, propylene glycol), vitamins, keratolytic agents and/or desquamating agents (salicylic acid and its derivatives, α-hydroxy acids, ascorbic acid and its derivatives), anti-inflammatory agents, calmants and mixtures thereof can be used in particular as active agents. The aminophenol derivatives can also be combined with other depigmenting agents, such as kojic acid or hydroquinone and its derivatives, which allows the latter agents to be used at doses that are less toxic to the skin. In the event of incompatibility, these active agents and/or the aminophenol derivatives can be incorporated into spherules, in particular ionic or non-ionic vesicles and/or nanoparticles (nanocapsules and/or nanospheres), so as to isolate them from each other in the composition.

The invention will now be illustrated with the aid of the examples which follow. The concentrations are given as a percentage by weight.

EXAMPLES OF COMPOUNDS

Example 1
N-Ethyloxycarbonyl-4-aminophenol 20 g of 4-aminophenol (Mw=109.13; 0.18324 mol) are suspended in 200 cm$^3$ of anhydrous dichloromethane, under an inert atmosphere. The suspension is cooled to a temperature of 0° C. in a bath of ice and 16.4 cm$^3$ of anhydrous pyridine (Mw=79.10; d=0.981; 0.2034 mol) are then added. 17.6 cm$^3$ of ethyl chloroformate (Mw=108.53; d=1.13; 0.18324 mol) are then added dropwise so as to keep the mixture at a temperature below 10° C. The reaction mixture is kept stirring for two hours. The mixture is poured onto one liter of ice-cold water and then extracted with ethyl acetate. The organic phase is washed with water and then dried, filtered and evaporated under vacuum. After recrystallization from a heptane/ethyl acetate mixture, 21 g of a white powder are obtained, which corresponds to a yield of 63%. The melting point of the product obtained is 127.2° C. The H NMR spectrum and the elemental analysis are in accordance with the expected product.

Example 2
N-Ethyloxycarbonyl-O-ethyloxycarbonyl-4-aminophenol 10 g of 4-aminophenol (Mw=109.13; 0.0916 mol) are suspended in 100 cm$^3$ of anhydrous dichloromethane, under an inert atmosphere. The suspension is cooled to a temperature of 0° C. in a bath of ice and 8.2 cm$^3$ of anhydrous pyridine (Mw=79.10; d=0.981; 0.102 mol) are then added. 9.8 cm$^3$ of ethyl chloroformate (Mw=108.53; d=1.13; 0.104 mol) are then added dropwise so as to keep the mixture at a temperature below 10° C. The reaction mixture is kept stirring for two hours. The mixture is poured onto one liter of ice-cold water and then extracted with ethyl acetate. The organic phase is washed with water and then dried, filtered and evaporated under vacuum. After recrystallization from ethanol, 18 g of a white powder are obtained, which corresponds to a yield of 80%. The melting point of the product obtained is 110.8° C. The 200 MHz $^1$H NMR spectrum and the elemental analysis are in accordance with the expected product.

Example 3
N-Cholesteryloxycarbonyl-4-aminophenol 21.8 g of 4-aminophenol (Mw=109.13; 0.2 mol) are suspended in 200 cm$^3$ of anhydrous N,N-dimethylacetamide under an inert atmosphere. 44.9 g of cholesteryl chloroformate (Mw=449.11; 0.1 mol) are then added dropwise so as to keep the temperature below 30° C. The reaction mixture is kept stirring for two hours. The mixture is poured onto five liters of water and the precipitate is then filtered off and dried. After recrystallization from a water/ethanol mixture, 46 g of a white powder are obtained, which corresponds to a yield of 88%. The melting point of the product obtained is 186.9° C. The 100 MHz $^{13}$C NMR spectrum and the elemental analysis are in accordance with the expected product.

Example 4
N-Ethylaminocarbonyl-4-aminophenol 10 g of 4-aminophenol (Mw=109.13; 0.0916 mol) are suspended in 100 cm$^3$ of anhydrous N-methylpyrrolidone, under an inert atmosphere. 6.5 g of ethyl isocyanate (Mw 71.08; 0.0914 mol) are then added dropwise. The reaction mixture is brought to a temperature of 60° C. with stirring for two hours. The mixture is poured into one liter of water and the precipitate is then filtered off and dried. After recrystallization from ethanol., 9 g of a white powder are obtained, which corresponds to a yield of 55%. The melting point of the product obtained is 173.4° C. The 200 MHz $^1$H NMR spectrum and the elemental analysis are in accordance with the expected product.

Tests:

A biological test demonstrated the depigmenting activity of the aminophenol derivatives of formula (I).

This test corresponds to the one described in patent FR 2,734,825 filed by the Applicant, as well as in the article by R. Schmidt, P. Krien and M. Regnier, Anal. Biochem., 235(2), 113–18, (1996). This test s thus carried out on a co-culture of keratinocytes and melanocytes.

For each test compound, the IC$_{50}$ value, which corresponds to the micromolar ($\mu$M) concentration for which a 50% inhibition of melanogenesis is observed, is determined.

Moreover, each of these compounds is classed as regards their maximum depigmenting activity:

Class 1: 10 to 30% inhibition of melanogenesis relative to the control (same experiment without test compound);

Class 2: 30 to 60% inhibition of melanogenesis relative to the control (same experiment without test compound);

Class 3: 60 to 100% inhibition of melanogenesis relative to the control (same experiment without test compound).

The results are collated in Table (I) below.

|  | IC$_{50}$ ($\mu$M) | Class |
|---|---|---|
| Compound of Example 1 | 1 | 3 to 1 $\mu$M |
| Compound of Example 2 | 50 | 3 to 200 $\mu$M |
| Compound of Example 3 | 10 | 3 to 200 $\mu$M |
| Kojic acid | 500 | 2 to 500 $\mu$M |

These compounds of formula (I) thus have greater depigmenting efficacy than kojic acid. In addition, they have the advantage of not being cytotoxic with regard to keratnocytes and melanocytes, which is the major fault of the existing depigmenting agents.

Examples of Compositions

Example 5

Treating Cream

| | |
|---|---|
| Cetyl alcohol | 1.05% |
| PEG-20 stearate (Myrj 49 sold by the company ICI) | 2% |
| Cyclomethicone | 6% |
| Compound of Example 1 | 0.5% |
| Carbomer | 0.6% |
| Glycerol | 3% |
| Triethanolamine | 1% |
| Preserving agents | 0.5% |
| Demineralized water qs | 100% |

When applied daily, the cream obtained allows the skin to be bleached.

Example 6

Treating Gel

| | |
|---|---|
| Propylene glycol | 10% |
| Ethyl alcohol | 40% |
| Glycerol | 3% |
| Compound of Example 2 | 0.5% |
| Preserving agents | 0.15% |
| Fragrance | 0.15% |
| Demineralized water qs | 100% |

The gel obtained can be used daily and is capable of depigmenting the skin.

Example 7

Treating Stick

| | |
|---|---|
| Carnauba wax | 5% |
| Ozokerite | 7% |
| Lanolin | 6% |
| Titanium dioxide (pigments) | 20% |
| Rice starch (filler) | 7% |
| EDTA | 0.1% |
| Compound of Example 3 | 2% |
| Perhydrosqualene qs | 100% |

When used on pigmentation marks, the stick obtained makes them fade, or even disappear altogether.

What is claimed is:

1. An aminophenol compound represented by formula (I):

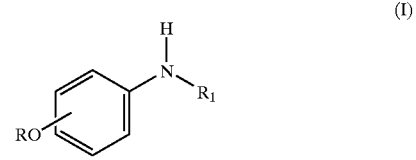

(I)

wherein
R represents—COR$_2$,
R$_2$ represents isopropyl, t-butyl, 2-ethylhexyl, 2-butyloctyl, 2-hexadecyl, neryl, 2-nonyl-2-butenyl, 6-(1,3-pentadienyl)-2,4,7-dodecatrien-9-ynyl, allyl, hydroxymethyl, 2-hydroxyethyl, 2-hydroxypropyl, 3-hydroxypropyl, 2,3-dihydroxypropyl, 2,3,4-trihydroxypropyl, 2,3,4-trihydroxybutyl, 2,3,4,5-tetrahydroxypentyl or 2,3,4,5,6-pentahydroxyhexyl; and
R$_1$ is a cholesteryloxycarbonyl radical.

2. The aminophenol compound according to claim 1, wherein R$_2$ is selected from the group consisting of isopropyl, t-butyl, 2-ethylhexyl, 2-butyloctyl and 2-hexadecyl.

3. The aminophenol compound according to claim 1, wherein R$_2$ is selected from the group consisting of neryl, 2-nonyl-2-butenyl, 6-(1,3-pentadienyl)-2,4,7-dodecatrien-9-ynyl and allyl.

4. The aminophenol compound according to claim 1, wherein R$_2$ is selected from the group consisting of hydroxymethyl, 2-hydroxyethyl, 2-hydroxypropyl and 3-hydroxypropyl.

5. The aminophenol compound according to claim 1, wherein R$_2$ is selected from the group consisting of 2,3-dihydroxypropyl, 2,3,4-trihydroxypropyl, 2,3,4-trihydroxybutyl, 2,3,4,5-tetrahydroxypentyl and 2,3,4,5,6-pentahydroxyhexyl.

6. A method of depigmenting and/or bleaching human skin, body hairs or head hair, comprising applying to human skin, body hairs or head hair the aminophenol compound as claimed in claim 1.

7. A cosmetic and/or dermatological composition, comprising:
the aminophenol compound as claimed in claim 1; and
a cosmetically and/or dermatologically acceptable medium.

8. A method of making a cosmetic and/or dermatological composition comprising:
combining the aminophenol compound as claimed in claim 1 and a cosmetically and/or dermatologically acceptable medium.

9. A method of depigmenting and/or bleaching human skin, body hairs or head hair, comprising applying to human skin, body hairs or head hair N-cholesteryloxycarbonyl-4-aminophenol.

10. A cosmetic and/or dermatological composition, comprising:
N-cholesteryloxycarbonyl-4-aminophenol; and
a cosmetically and/or dermatologically acceptable medium.

11. A method of making a cosmetic and/or dermatological composition comprising:
combining N-cholesteryloxycarbonyl-4-aminophenol and a cosmetically and/or dermatologically acceptable medium.

12. The method of claim 9, comprising applying said N-cholesteryloxycarbonyl-4-aminophenol to human skin.

13. The method of claim 12, comprising applying said N-cholesteryloxycarbonyl-4-aminophenol to human skin to bleach said skin.

14. The method of claim 12, comprising applying said N-cholesteryloxycarbonyl-4-aminophenol to human skin to depigment said skin.

15. The method of claim 9, wherein said N-cholesteryloxycarbon-4-aminophenol is present in a composition in an amount ranging from 0.005% to 5% of the total weight of the composition.

16. The method of claim 12, wherein said N-cholesteryloxycarbonyl-4-aminophenol is present in a composition in an amount ranging from 0.005% to 5% of the total weight of the composition.

17. The method of claim 13, wherein said N-cholesteryloxycarbonyl-4-aminophenol is present in a composition in an amount ranging from 0.005% to 5% of the total weight of the composition.

18. The method of claim 14, wherein said N-cholesteryloxycarbonyl-4-aminophenol is present in a composition in an amount ranging from 0.005% to 5% of the total weight of the composition.

* * * * *

UNITED STATES PATENT AND TRADEMARK OFFICE
CERTIFICATE OF CORRECTION

PATENT NO. : 6,924,275 B2
DATED : August 2, 2005
INVENTOR(S) : Michel Philippe et al.

It is certified that error appears in the above-identified patent and that said Letters Patent is hereby corrected as shown below:

Title page,
Item [57], ABSTRACT,
Line 14, "wherein $R_3$ represents a hydrogen atom or a linear or branched, saturated or unsaturated, optionally hydroxylated, $C_1$ to $C_4$ hydrocarbon radical," should read -- wherein $R_3$ represents a hydrogen atom or a linear or branched, saturated or unsaturated, optionally hydroxylated, $C_1$ to $C_6$ hydrocarbon radical, --.

Signed and Sealed this

First Day of November, 2005

JON W. DUDAS
*Director of the United States Patent and Trademark Office*